(12) United States Patent
Okada

(10) Patent No.: US 7,008,420 B2
(45) Date of Patent: Mar. 7, 2006

(54) HIGH FREQUENCY SURGICAL INSTRUMENT

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/730,818

(22) Filed: Dec. 9, 2003

(65) Prior Publication Data

US 2004/0153059 A1    Aug. 5, 2004

(30) Foreign Application Priority Data

Dec. 12, 2002  (JP)  .............................. 2002-361163

(51) Int. Cl.
*A61B 18/18*   (2006.01)
(52) U.S. Cl. ............................ 606/47; 606/41; 606/45; 606/46; 607/99; 607/101; 607/115
(58) Field of Classification Search ................ 606/41, 606/45, 46, 47; 607/99, 101, 115
See application file for complete search history.

(56) References Cited

U.S. PATENT DOCUMENTS

| 4,256,113 A | 3/1981 | Chamness |
| 5,066,295 A * | 11/1991 | Kozak et al. ................. 606/47 |
| 5,769,880 A | 6/1998 | Truckai et al. |

FOREIGN PATENT DOCUMENTS

| JP | 55-173307 | 12/1980 |
| JP | 61-18885 | 6/1986 |
| JP | 2000-197643 | 7/2000 |

* cited by examiner

*Primary Examiner*—Rosiland Rollins
(74) *Attorney, Agent, or Firm*—Scully, Scott, Murphy & Presser

(57) ABSTRACT

The high frequency surgical instrument includes the electrical connection portion configured to detachably connect the connection cord designed for an external high frequency power source, to the slider, and the instrument has such a structure in which the contact pin configured to lead the connection cord backward in substantially parallel with the advancing and retreating direction of the slider is provided in substantially parallel with the advancing and retreating direction of the slider while the connection cord is connected to the electric connection portion.

4 Claims, 8 Drawing Sheets

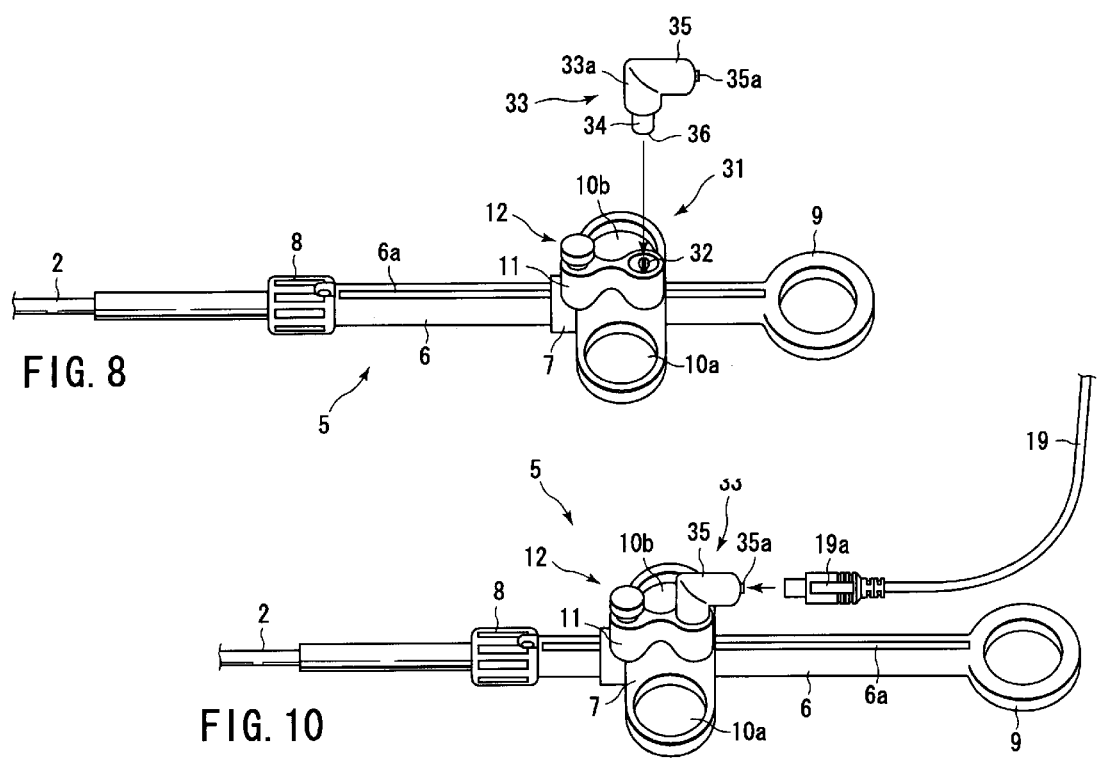

HIGH FREQUENCY SURGICAL INSTRUMENT

CROSS-REFERENCE TO RELATED APPLICATIONS

This application is based upon and claims the benefit of priority from the prior Japanese Patent Application No. 2002-361163, filed Dec. 12, 2002, the entire contents of which are incorporated herein by reference.

BACKGROUND OF THE INVENTION

1. Field of the Invention

The present invention relates to a high frequency surgical instrument to be used in combination with an endoscope, for performing a high frequency surgical operation at a high frequency current.

2. Description of the Related Art

The diathermic snare is a generally known example of the high frequency surgical instrument, which is inserted into a body cavity, for example, through a channel of an endoscope to perform a high frequency surgical operation on living tissue in the body cavity by allowing a high frequency current to flow in the instrument. The diathermic snare includes a snare loop made by folding a wire over into a loop shape and a plastic sheath. The snare loop is pierced through the plastic sheath such that it can be put into it and out. Then, living tissue in the body cavity is put into the snare loop and the loop is narrowed down while keeping the tissue within the loop, thereby tightening the living tissue. Then, a high frequency current is allowed to flow through the snare loop, and thus the fastened living tissue is cut.

The handle portion of the diathermic snare is made of a main body thereof and a slider. To the main body of the handle portion, a proximal end of the plastic sheath is mounted. The slider can move forward and backward on the main body. An operation wire is connected by its distal end to the snare loop, and the proximal end of the operation wire is connected to the slider. As the slider is moved forward and backward by manipulation, the snare loop can be put in and out of the plastic sheath by means of the operation wire.

Meanwhile, Jpn. U.M. Appln. KOKAI Publication No. 55-173307 (Patent Document 1) and U.S. Pat. No. 4,256,113 (Patent Document 2) disclose another structure of the diathermic snare. According to this structure, a connector is provided for the slider. A connection cord for an external high frequency current supply device is connected to the connector. With this structure, a high frequency current is supplied to the snare loop.

Jpn. Pat. Appln. KOKAI Publication No. 2000-197643 (Patent Document 3) and U.S. Pat. No. 5,769,880 (Patent Document 4) disclose another structure in which a finger placing portion in which the operator put a finger, is provided in the slider. Patent Document 3 discloses a structure in which the connector is provided to project vertically to the axial direction of the slider. Meanwhile, the device of Patent Document 4 has a structure in which the connector is provided to project at an angle with respect to the axial direction of the slider.

U.S. Pat. No. 5,066,295 (Patent Document 5) discloses a diathermic snare that includes a knob for rotating the snare loop at this handle portion. The slider has a connector. This document describes a structure in which as the knob is rotated with respect to the slider, the direction of the snare loop is changed to a desired direction by rotating the snare loop.

Further, Jpn. U.M. Application KOKOKU Publication No. 61-18885 (Patent Document 6) discloses a structure in which the snare loop is rotated by turning the entire handle portion.

BRIEF SUMMARY OF THE INVENTION

According an aspect of the present invention, there is provided a high frequency surgical instrument comprising: a slender cylindrical electro-insulating sheath including a distal end and a proximal end; a handle main body mounted to the proximal end of the sheath; a slider configured to advance and retreat on the handle main body along an axial direction of the sheath; an electrode portion for a diathermic treatment, configured to operate in accordance with operating of the slider; an electric connection portion provided in the slider, to which a connection cord for connection with an external high frequency power source, is detachably connected; a conducting member configured to electrically connecting the electric connection portion and the electrode portion; and a cord connection portion configured to lead the connection cord backwards along an advancing and retreating direction of the slider.

According another aspect of the present invention, there is provided a high frequency surgical instrument comprising: a slender cylindrical electro-insulating sheath including a distal end and a proximal end; a handle main body mounted to the proximal end of the sheath; a slider configured to advance and retreat on the handle main body along an axial direction of the sheath; an electrode portion for a diathermic treatment, configured to project from or withdraw into a distal end of the sheath in accordance with the advancing and retreating of the slider; an electric connection portion provided in the slider, to which a connection cord for connection with an external high frequency power source, is detachably connected; a conducting member configured to electrically connecting the electric connection portion and the electrode portion; and a cord connection portion configured to lead the connection cord backwards along an advancing and retreating direction of the slider.

It is preferable that the electric connection portion should include a connection portion rotating means configured to connect the connection cord thereto rotatably in the direction of rotation of the axis of the connection cord.

It is preferable that the electric connection portion should include a plug to which the connection cord can be mounted, the plug include a contact pin and the contact pin should be provided in parallel with the advancing and retreating direction of the slider.

It is also preferable that the electric connection portion should further comprise: a vertical plug projecting in a vertical direction that is normal to the advancing and retreating direction of the slider; and a direction-changing plug configured to change a direction of the plug in a direction in parallel to the advancing and retreating direction of the slider, the plug being coupled detachably to the vertical plug; the vertical plug should include a contact pin projecting in a vertical direction that is normal to the advancing and retreating direction of the slider; the direction-changing plug should include a plug main body having a shape bent into substantially a letter L; the plug main body should further include: a main body-side connection portion projecting from one of the bent shape of the letter L; and a cord-side connection portion projecting from an other one of the bent shape of the letter L; and the cord connection portion should include a contact pin formed to project in substantially parallel with the advancing and retreating direction of the slider, and to which the connection cord is detachably connected.

It is preferable that the electric connection portion should include a vertical plug formed to project in a vertical direction that is normal to the advancing and retreating direction of the slider, and the connection cord should include an L-shaped connector detachably connected to the vertical plug, the connector being bent into substantially an L-shape.

Advantages of the invention will be set forth in the description which follows, and in part will be obvious from the description, or may be leaned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8 is a perspective view of the main part of a diathermic snare according to the second embodiment of the present invention;

FIG. 10 is a perspective diagram showing the handle portion in a state before the connector of the cord is connected to the plug of the slider in the diathermic snare according to the second embodiment;

DETAILED DESCRIPTION OF THE INVENTION

Figure 1:
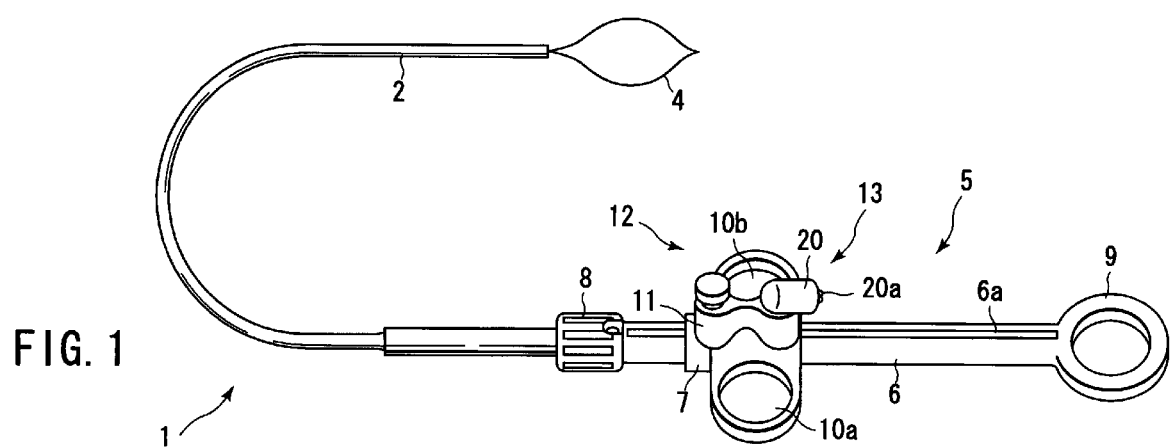
FIG. 1 is a perspective view illustrating an appearance of a diathermic snare according to the first embodiment.
Figure 2:
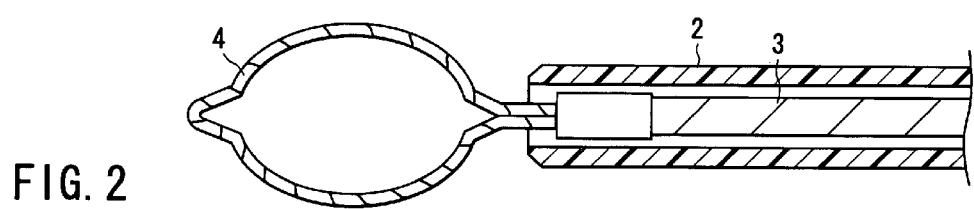
FIG. 2 is a diagram showing a longitudinal section of a main part of a distal end portion of the diathermic snare according to the first embodiment, which is designed to illustrate an internal structure of the distal end portion.

The first embodiment of the present invention will now be described with reference to FIGS. 1 to 7A. FIG. 1 shows a diathermic snare 1 serving as a high frequency surgical instrument of this embodiment. The diathermic snare 1 includes a slender electrical insulating flexible tube (electrical insulating sheath) 2, and an operation wire 3 pierced through the flexible tube 2 to be advanceable and retreatable. To a distal end of the operation wire 3, a snare loop (electrode portion for a diathermic treatment) 4 formed by folding a wire into a loop shape is connected. With this structure, the snare loop 4 is operated to project and retreat from the distal end of the flexible tube 2 as the operation wire 3 is advanced or retreated. During this operation, as the snare loop 4 projects or retreats from the distal end of the flexible tube 2, the loop 4 expands or contracts, respectively, due to the elasticity of the loop itself. More specifically, when the operation wire 3 is pulled to the handling side, the snare loop 4 is inserted into the flexible tube 2, thus reducing the size of the loop. On the other hand, the operation wire 3 is pushed out forwards, the snare loop 4 is projected out from the distal end of the flexible tube 2, thus expanding the loop.

A proximal end of the flexible tube 2 is provided with a handle portion 5. The handle portion 5 includes a substantially shaft-shaped main body 6 of the handle portion, and a slider 7. The slider 7 is mounted on the main body 6 of the handle portion so as to be slidable along the direction of the axial like of the flexible tube 2. The distal end of the main body 6 is provided with a substantially cylindrical shaped flexible tube connection portion 8. The proximal end portion of the flexible tube 2 is mounted to the flexible connection portion 8 so as to be detachable therefrom and rotatable in the direction of the rotation axis. A rear end of the main body 6 of the handle portion is formed into a thumb operation ring 9.

A linear guide groove 6a is made in the main body 6 of the handle portion along its axial direction. The guide groove 6a is made between the flexible tube connection portion 8 and the thumb operation ring 9 such as to be in parallel with a central axis O of the main portion 6 of the handle portion, that is, in parallel with the advancing/retreating direction of the slider 7.

Figure 4:
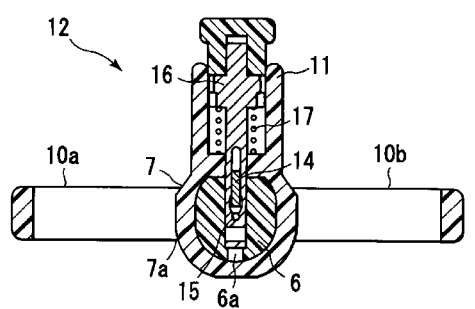
FIG. 4 is a diagram showing a cross section taken along the line IV—IV in FIG. 3.

Further, as shown in FIG. 4, the slider 7 has a hole 7a, through which the main body 6 of the handle portion is pierced. The slider 7 also has finger rings 10a and 10b formed in the right and left sides thereof. The rings 10a and 10b are formed to extend in both directions normal to the axial direction of the hole 7a.

Figure 3:
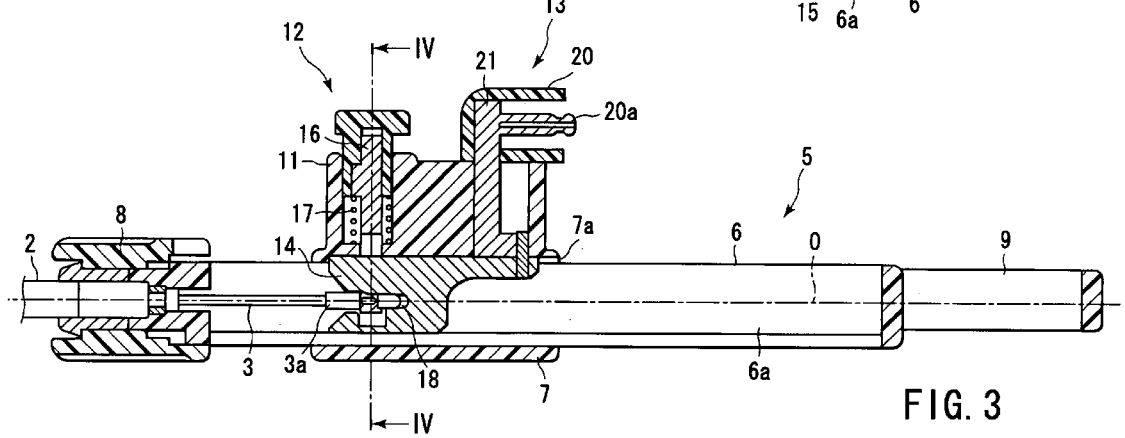
FIG. 3 is a diagram showing a longitudinal section of a main part of a handle portion of the diathermic snare according to the first embodiment, which is designed to illustrate an internal structure of the handle portion.

The slider 7 has a projecting portion 11. The projection portion 11 is projecting in a direction normal to the extending directions of the right and left finger rings 10a and 10b, that is, the upward direction above the hole 7a in FIGS. 3 and 4. The projecting portion 11 is provided with a wire connection device 12 and an electrical connection portion 13. As shown in FIG. 3, the projecting portion 11 has a contact member 14 (electro-conductive portion) made of a conductive material, at its lower section. The contact portion 14 is inserted into the guide groove 6a of the main body 6 of the handle portion.

As shown in FIG. 4, the wire connection device 12 is provided with a lock member 16 and a coil spring 17. The lock member 16 has a wire insertion hole 15 at its lower end section. The coil spring 17 serves to urge the lock member 16 in the upward direction in FIG. 4. The lower end section of the lock member 16 is inserted to the contact member 14 as shown in FIG. 3.

Further, the contact member 14 has a wire insertion hole 18. In to the wire insertion hole 18, a proximal end portion 3a of the operation wire 3 is inserted removably. Then, to mount the operation wire 3, the lock member 16 is pushed in against the spring force of the coil spring 17. While maintaining this state, the proximal end portion 3a of the operation wire 3 is inserted to the wire insertion hole 18 of the contact member 14, and then into the wire insertion hole 15 of the lock member 16. After that, when the lock member 16 is released from being pushed in, the lock member 16 is pushed out upwards in FIG. 4 by the coil spring 17 of the lock member 16. With this structure, the proximal end portion 3a of the operation wire 3 is detachably mounted to the connection device 12. During this period, the proximal end portion 3a of the operation wire 3 is maintained to be in contact with the contact portion 14.

Figure 5A:
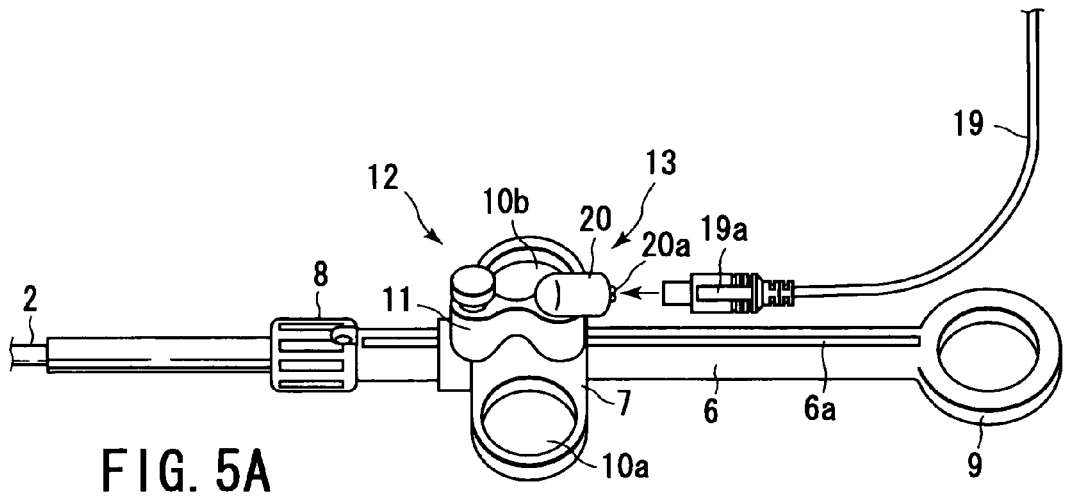
FIG. 5A is a perspective diagram showing the handle portion in a state before the connector of the cord is connected to the plug of the slider in the diathermic snare according to the first embodiment.
Figure 5B:
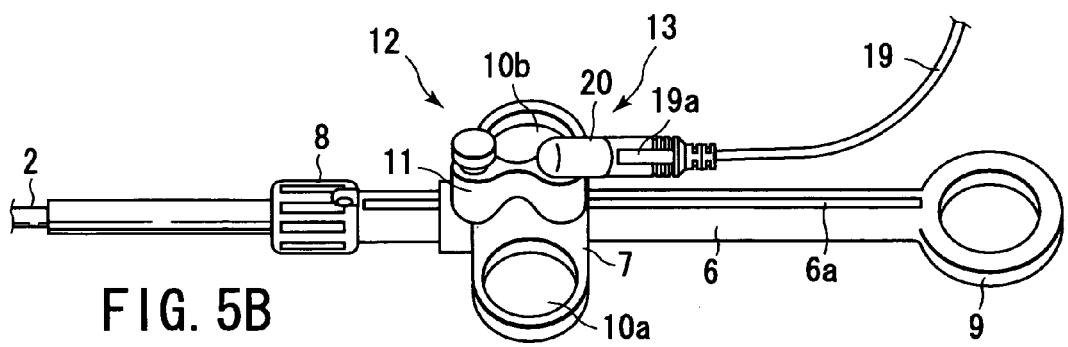
FIG. 5B is a perspective diagram showing the handle portion in a state in which the connector of the cord is connected to the plug of the slider.

The electric connection portion 13 has a plug 20. To the plug 20, a connection cord 19 (see FIGS. 5A and 5B) is detachably connected in order to connect the apparatus to an external high frequency power source, which is not shown in the figure. As shown in FIG. 3, a contact pin (cord parallel connection portion) 20a is provided in the plug 20. The connection pin 20a is made to project in substantially parallel to the advancing/retreating direction of the slider 7. A connector 19a provided at the distal end of the connection cord 19 is made detachably connectable to the contact pin 20a as it is fit with the pin. With this structure, as the connector 19a of the connection cord 19 is connected to the contact pin 20a, the connection cord 19 is lead backwards in substantially parallel to the advancing/retreating direction of the slider 7 as shown in FIG. 5B.

A proximal end portion of the contact pin 20a is fixed to a conducting member 21. A lower end portion of the conducting member 21 is fixed to the contact member 14. Thus, the contact pin 20a is electrically connected to the contact member 14 via the conducting member 21.

Next, the application of the above-described structure will now be described. Here, the description will be made in connection with the case of an operation of removing a polyp P shown in FIG. 6A with use of the diathermic snare 1 of this embodiment. For the operation, first, the proximal end portion of the flexible tube 2 is mounted to the flexible tube connection portion 8 of the main body 6 of the handle portion so as to be detachable and rotatable in the direction of the rotation axis. Then, the proximal end portion 3a of the operation wire 3 is detachably mounted to the wire connection device 12 of the slider 7 in the handle portion 5.

Subsequently, the connector 19a of the connection cord 19, which is designed for connection with an external high frequency power source not shown in the figure, is fit to the contact pin 20a projecting in substantially parallel with the advancing/retreating direction of the slider 7.

After that, as the slider 7 of the diathermic snare 1 is pulled to the handling side, the snare loop 4 is set within the flexible tube 2. While maintaining this state, the flexible tube 2 of the diathermic snare 1 is inserted to a body cavity through the channel 23 of the endoscope 22 as shown in FIG. 6A.

Then, the distal end portion of the flexible tube 2 is guided to a position close to the polyp P, which is the object to be surgically treated. While maintaining this state, the slider 7 of the handle portion 5 is operated to advance, and thus the operation wire 3 is pushed forward. As the operation wire 3 is pushed, the snare loop 4 is pushed out as well to project from the distal end of the flexible tube 2. As it projects out, the loop is expanded.

Figure 6A:
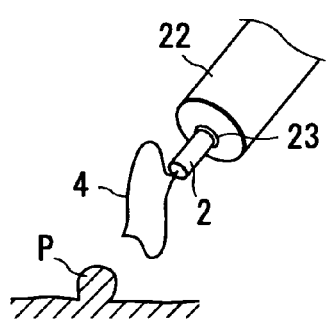
FIG. 6A is a perspective diagram showing the main part of the diathermic snare in such a state that the snare loop is projecting in a direction in which it is hard to hook the loop around a polyp when the direction of the snare loop of the diathermic snare according to the first embodiment is corrected.
Figure 6B:
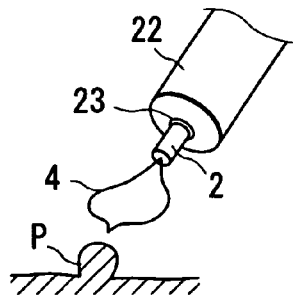
FIG. 6B is a perspective diagram showing the main part of the diathermic snare in such a state that the direction of the snare loop is corrected in a direction in which it is easy to hook the loop around a polyp.
Figure 7A:
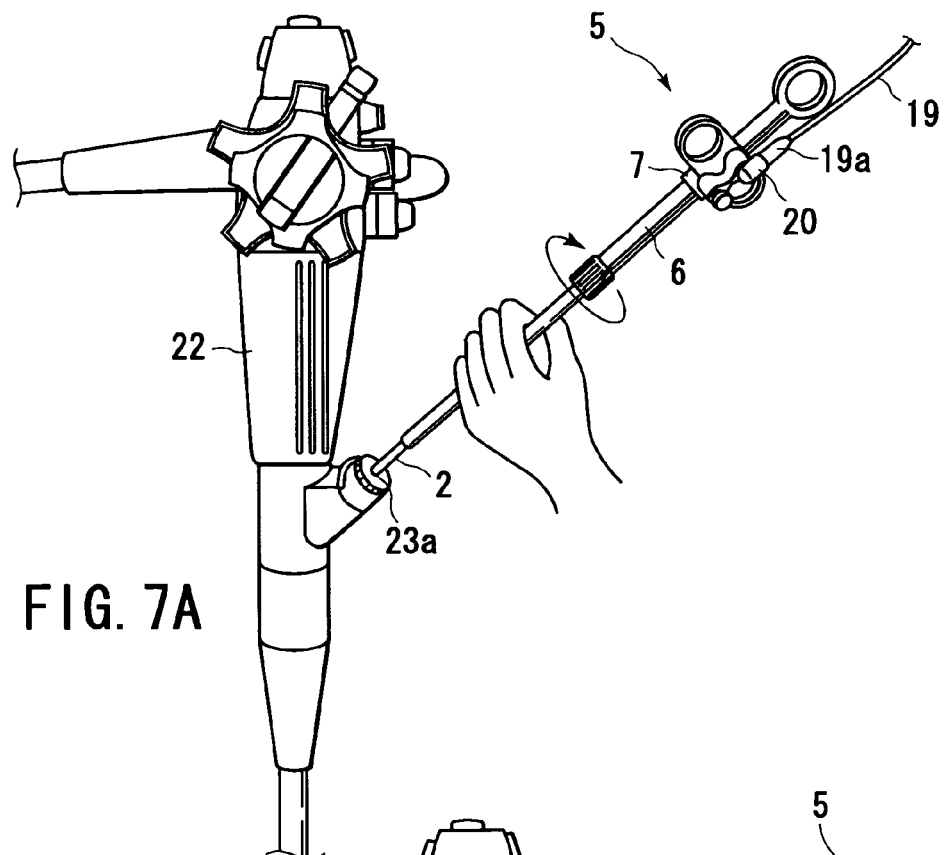
FIG. 7A is a perspective view of a peripheral portion of the handle portion, designed to explain the operation on the handle portion side, for correcting the direction of the snare loop of the diathermic snare according to the first embodiment.

During this operation, if the snare loop 4 projects in such a direction that it cannot be easily hooked around the polyp P, that is, for example, if the opening surface of the snare loop 4 is directed in substantially parallel with the protruding direction of the polyp P as shown in FIG. 6A, the flexible tube 2 is held and the entire handle portion 5 is rotated in the direction of the rotation axis as shown in FIG. 7A. Thus, the direction of the snare loop 4 is corrected in such a direction that the loop can be easily hooked around the polyp P, that is, for example, the opening surface of the snare loop 4 is re-directed in the direction substantially normal to the protruding direction of the polyp P.

After that, the polyp P is inserted into the snare loop 4 and then the polyp P is captured. While maintaining this state, the slider 7 is pulled in the retreating direction to the handling side, thus withdrawing the snare loop 4 into the flexible tube 2. In this manner, the polyp P is tightened by its root section. Subsequently, while maintaining this state, a high-frequency current is allowed to flow to the snare loop 4, and thus the polyp P can be removed.

An instrument with the above-described structure has the following advantage. That is, the diathermic snare 1 of the above embodiment has the contact pin 20a formed to project in substantially parallel with the advancing/retreating direction of the slider 7, in the plug 20 provided for the electric connection portion 13 of the slider 7. With this structure, the central axis of the plug 20 to which the cord 19 is to be connected is set in parallel with the central axis O of the main body 6 of the handle portion. Therefore, when the connector 19a of the connection cord 19 is detachably fit to the contact pin 20a, the connection cord 19 is lead out backwards in substantially parallel with the advancing/retreating direction of the slider 7 while the connector 19a of the connection cord 19 is connected to the contact pin 20a. With this arrangement, even if the entire handle portion 5 is rotated in a direction of the rotation axis to change the direction of the snare loop 4 in a desired direction for capturing tissue in a body cavity, the cord 19 is prevented from entwining the handle portion 5.

Figure 7B:
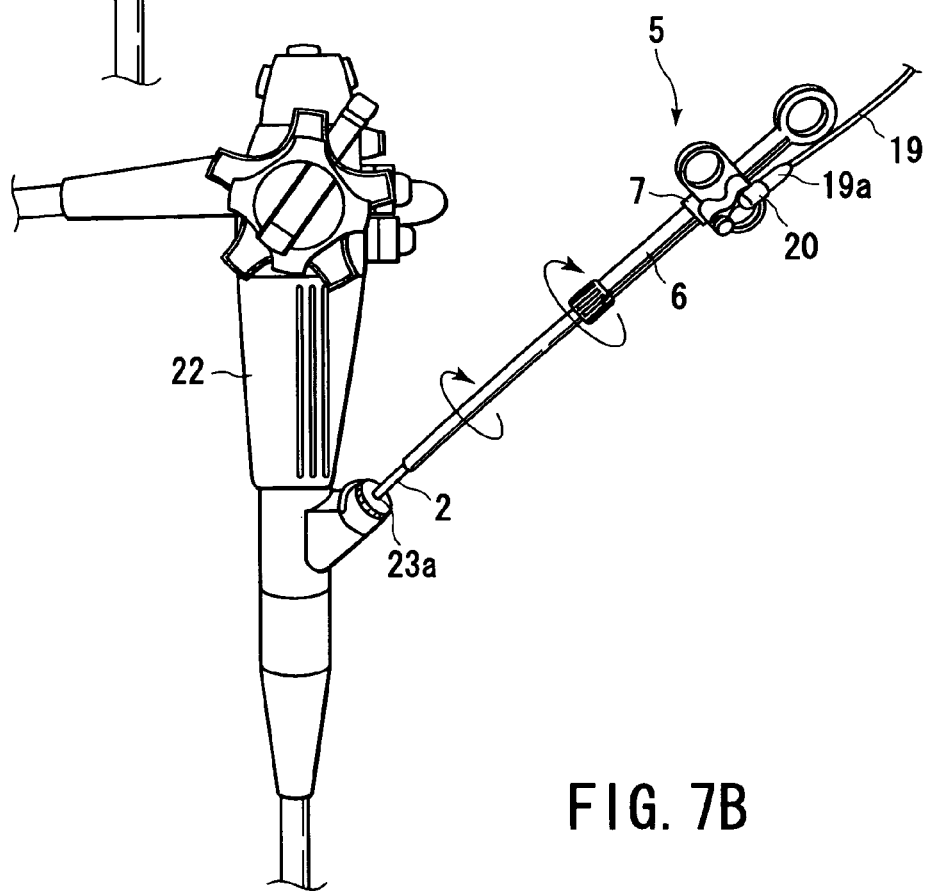
FIG. 7B is an explanatory diagram illustrating the operation of rotating the entire handle portion and flexible tube in an alternative version of the diathermic snare according to the first embodiment.

Apart from the above, in some cases, the flexible tube 2 is non-rotatably mounted to the flexible tube connection portion 8 of the main body 6 of the handle portion in the diathermic snare 1 of this embodiment. In such cases, it is possible to employ a structure in which the entire handle portion 5 and the flexible tube 2 are rotated at the same time in the same direction with respect to a forceps opening 23a communicating to the channel 23 of the endoscope 22 as shown in FIG. 7B.

Alternatively, the connection between the flexible tube connection portion 8 of the main body 6 of the handle portion and the proximal end portion of the flexible tube 2, and the connection between the proximal end portion 3a of the operation wire 3 and the slider 7 of the main body 6 of the handle portion are not necessarily detachable, but they may be integrated.

FIGS. 8 to 11 each illustrate the second embodiment of the present invention. This embodiment has such a configuration that the electric connection portion 13 of the diathermic snare 1 of the first embodiment (see FIGS. 1 to 7A) is changed to an electrical connection portion 31 that has the below-described structure. It should be noted here that the second embodiment has the same structure as that of the diathermic snare 1 of the first embodiment except for the structure of the electric connection portion 31, and therefore the parts similar to those of the diathermic snare 1 of the first embodiment are designated by the same reference numerals, and the explanations for these parts will not be repeated here.

Figure 9:
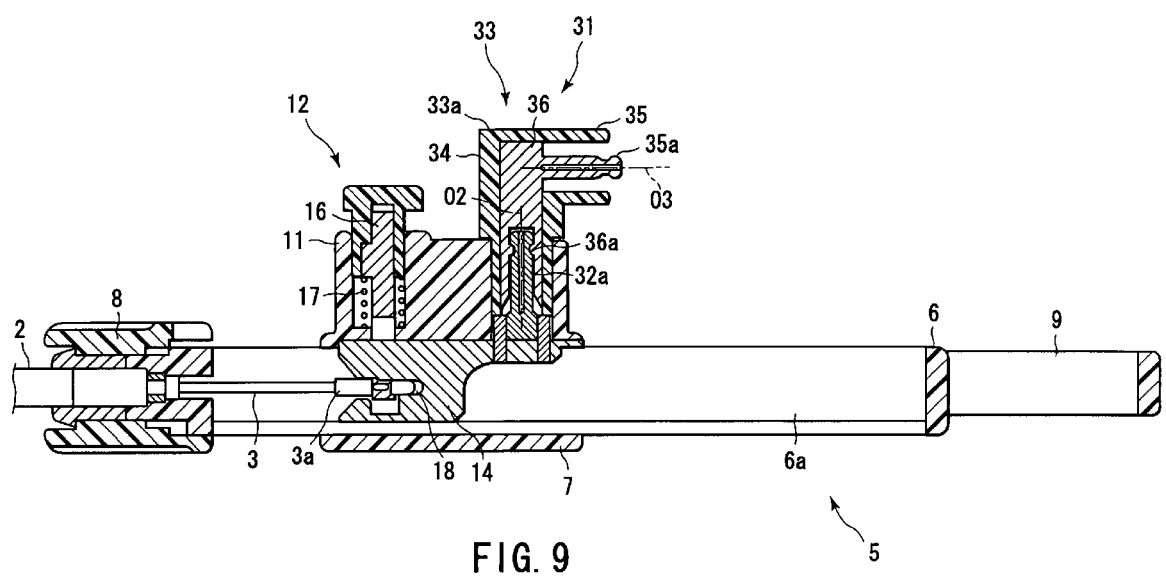
FIG. 9 is a diagram showing a longitudinal section of a main part of a handle portion of the diathermic snare according to the second embodiment, which is designed to illustrate an internal structure of the handle portion.

That is, in the diathermic snare 1 of this embodiment, a vertical plug 32 is provided for the electric connection portion 31 of the slider 7 as in the conventional technique. The plug 32 is formed to project in a vertical direction, which is normal to the advancing/retreating direction of the slider 7. As shown in FIG. 9, the vertical plug 32 has a contact pin 32a projecting in the vertical direction, which is normal to the advancing/retreating direction of the slider 7.

The vertical plug 32 is formed such that a conversion plug 33 is detachably connected thereto. The conversion plug 33 serves to change the direction of the plug 32 to be in parallel with the advancing direction of the slider 7. The conversion plug 33 has a plug main body 33a that is bent into substantially an L shape as shown in FIG. 8. In one end of the L shape of the plug main body 33a, a main body-side connection portion 34 is formed to project from that end. In another end of the L shape of the plug main body 33a, a cord-side connection portion 35 is formed to project from that end.

Further, the main body-side connection portion 34 has an engaging portion 36 that is electrically engaged with the contact pin 32a of the vertical plug 32. The engaging portion 36 has a pin insertion hole 36a, to which the contact pin 32a of the vertical plug 32 is inserted. As the contact pin 32a of the vertical plug 32 is inserted to the pin insertion hole 36a, the conversion plug 33 is detachably plugged to the vertical plug 32 to fit.

Further, in the cord-side connection portion 35, a contact pin (cord parallel connection portion) 35a is provided so as to project in substantially parallel with the advancing/retreating direction of the slider 7 as shown in FIG. 9. The proximal end portion of the contact pin 35a is fixed to the upper end portion of the engaging portion 36. In this manner, the contact pin 35a having a central axis O3 that is normal to a central axis O2 of the pin insertion hole 36a of the engaging portion 36 is integrally formed. Thus, the contact pin 35a has such a structure that the connector 19a of the connection cord 19 can be detachably fit therein for connection, as shown in FIG. 10.

Next, the operation of the above-described structure will now be described. The diathermic snare 1 of this embodiment is different from that of the first embodiment only in the following respect. That is, in this embodiment, the connector 19a of the cord 19 is connected to the vertical plug 32 of the slider 7 via the conversion plug 33 when the connection cord 19, which is used for the connection to an external high frequency power source, which is not shown in the figure, is to be connected to the electrical connection portion 31 of the handle portion 5.

The instrument having the above-described structure exhibits the following advantageous effect. That is, according to this embodiment, a substantially L-shaped conversion plug 33 is detachably mounted to the vertical plug 32 that is formed normal to the advancing/retreating direction of the slider 7. Thus, due to the conversion plug 33 set on the vertical plug 32 of the slider 7, the contact pin 32a of the vertical plug 32 can be re-directed to a direction in parallel to the advancing/retreating direction of the slider 7, which is in a direction of the contact pin 35a of the conversion plug 33, even with the handle portion 5 that has the vertical plug 32 formed normal to the direction in parallel to the advancing/retreating direction of the slider 7.

Figure 11:
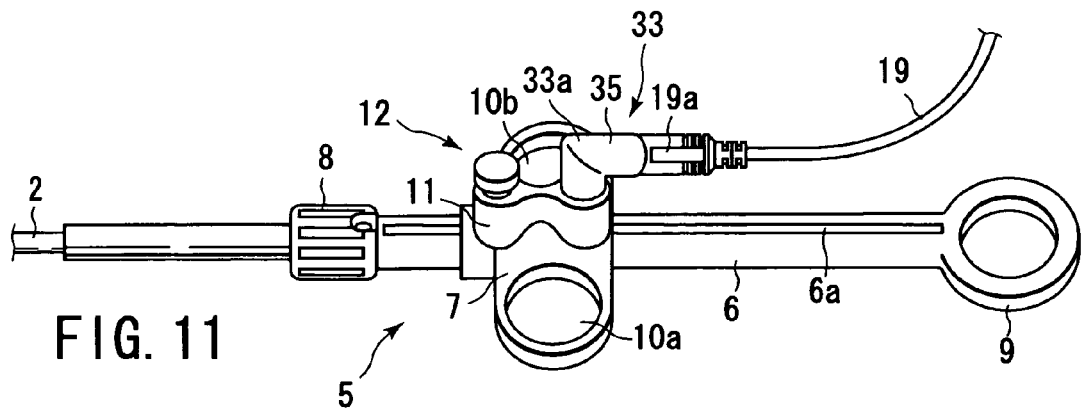
FIG. 11 is a perspective diagram showing the handle portion in a state in which the connector of the cord is connected to the plug of the slider in the diathermic snare according to the second embodiment.

Therefore, as the connector 19a of the connection cord 19 is detachably fit to the contact pin 35a of the conversion plug 33, the connection cord 19 can be lead backwards substantially in parallel with the advancing/retreating direction of the slider while the connector 19a of the connection cord 19 is connected to the contact pin 35a, as shown in FIG. 11. With this structure, it is able to prevent the cord 19 from entwining with the handle portion 5 even when the entire handle portion 5 is rotated in the direction of the rotation axis to change the direction of the snare loop 4 in a desired direction for capturing living tissue in a body cavity, as in the first embodiment.

Figure 12:
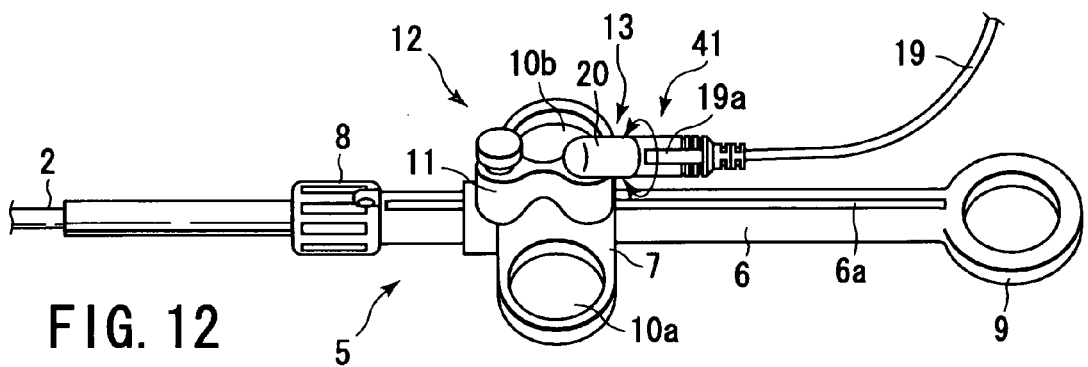
FIG. 12 is a perspective view of the main part of a diathermic snare according to the third embodiment of the present invention.

FIG. 12 shows the third embodiment of the present invention. In this embodiment, the electric connection portion 13 of the diathermic snare 1 of the first embodiment (see FIGS. 1 to 7A) is re-structured as will now be described.

That is, a rotation connection portion (connection portion rotation means) 41 to which the connector 19a of the connection code 19 is coupled rotatably in the direction of the rotation axis as indicated by arrows in FIG. 12, is formed at the connection portion between the contact pin 20a of the plug 20 of the diathermic snare 1 and the connector 19a of the connection cord 19 in the first embodiment.

The instrument having the above-described structure exhibits the following advantageous effect. That is, in this embodiment, the connector 19a is made rotatable with respect to the plug 20 in the direction of the rotation axis, while the connector 19a of the connection cord 19 is mounted to the plug 20 of the diathermic snare 1. With this structure, even if the cord 19 is twisted, the connector 19a of the connection cord 19 is rotated in the direction of the rotation axis with respect to the contact pin 20a of the plug 20 by the rotation connection portion 41. Thus, the cord 19 can be easily straightened and thus it is possible to avoid the twisting of the cord 19.

Figure 13:
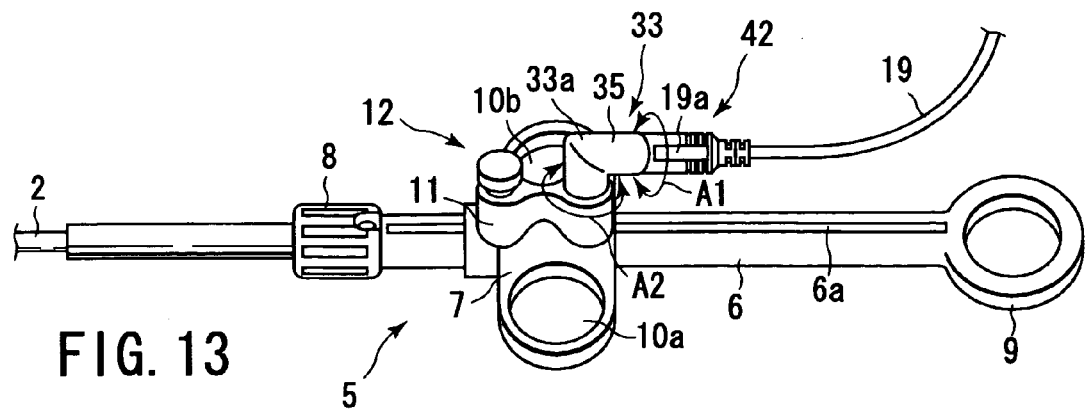
FIG. 13 is a perspective view of the main part of a diathermic snare according to the fourth embodiment of the present invention.

FIG. 13 shows the fourth embodiment of the invention. In this embodiment, the electric connection portion 31 of the diathermic snare 1 of the second embodiment (see FIGS. 8 to 11) is re-structured as will now be described.

That is, a first rotation connection portion (connection portion rotation means) 42 to which the connector 19a of the connection code 19 is coupled rotatably in the direction of the rotation axis as indicated by arrow A1 in FIG. 13, is formed at the connection portion between the contact pin 35a of the conversion plug 33 of the diathermic snare 1 and the connector 19a of the connection cord 19 in the second embodiment.

Further, the direction-changing plug 33 of this embodiment has such a structure as shown in FIG. 13. That is, the connection portion between the contact pin 32a of the vertical plug 32 and the engaging portion 36 of the main body-side connection portion 34 as in the second embodiment is equipped with a second rotation connection portion 42 to which the main body-side connection portion 34 of the direction-changing plug 33 is coupled rotatably in the direction of the rotation axis as indicated by arrow A2 in FIG. 13. Thus, in the conversion plug 33 of this embodiment, the main body-side connection portion 34 is coupled to the vertical plug 32 rotatably in the direction of the rotation axis, and the connector 19a of the connection cord 19 is coupled to the cord-side connection portion 35 rotatably in the direction of the rotation axis.

Therefore, the embodiment having the above-described structure exhibits the following advantageous effect. That is, even if the handle portion 5 of the diathermic snare 1 is moved, the cord 19 can be easily straightened and therefore the twisting can be easily disentangled.

Figure 14:
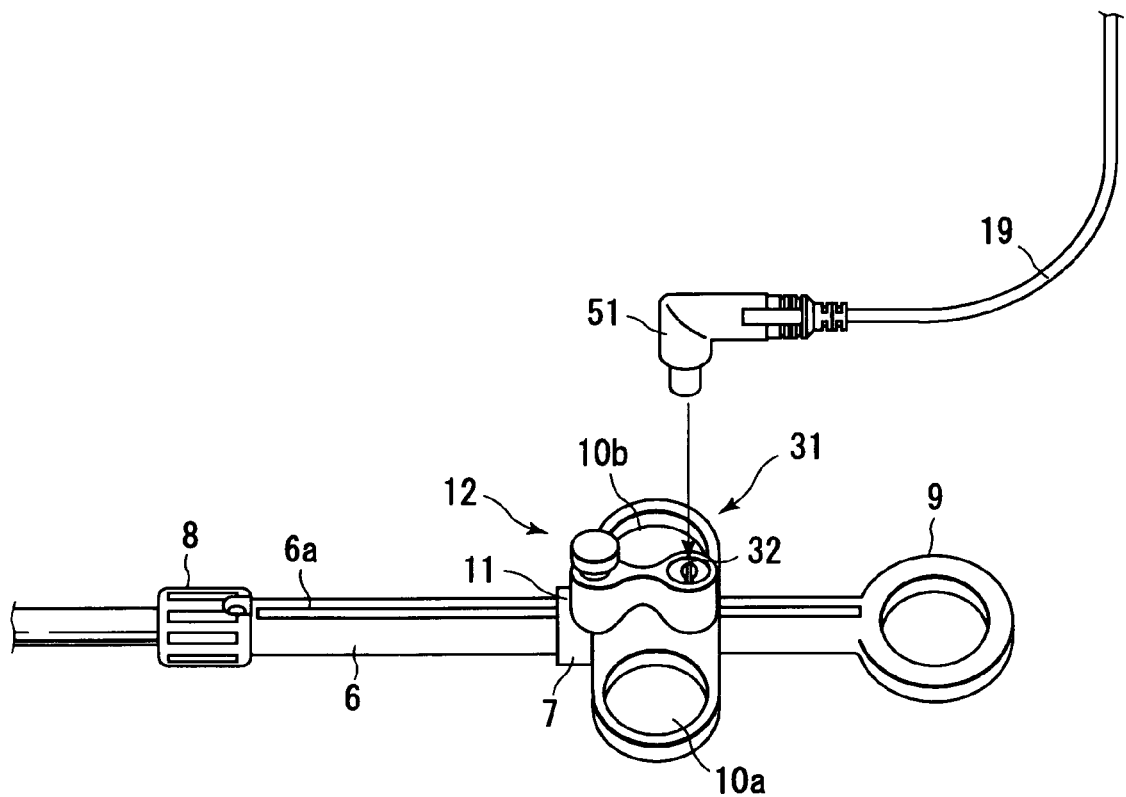
FIG. 14 is a perspective view of a main part of a handle portion of the diathermic snare according to the fifth embodiment, which is designed to illustrate the connection section between the plug of the slider and the connector of the cord.

FIG. 14 shows the fifth embodiment of the present invention. In this embodiment, the electric connection portion 31 of the diathermic snare 1 of the second embodiment (see FIGS. 8 to 11) is re-structured as will now be described.

That is, in this embodiment, an L-shaped connector 51 formed bent into a letter of substantially L is provided in place of the connector 19a of the cord 19 of the second embodiment, which is formed straight. The L-shaped connector 51 is mounted to the vertical plug 32 in the electric connection portion 31 of the diathermic snare 1 of the second embodiment, to fit therewith.

Thus, in this embodiment that has the above-described structure, when the L-shaped connector 51 is connected to the vertical plug 32 in the electric connection portion 31 of the diathermic snare 1 of the second embodiment, the cord 19 is set substantially in parallel with the advancing/retreating direction of the slider 7. Therefore, this embodiment exhibits an advantageous effect similar to that of the second embodiment.

Figure 15:
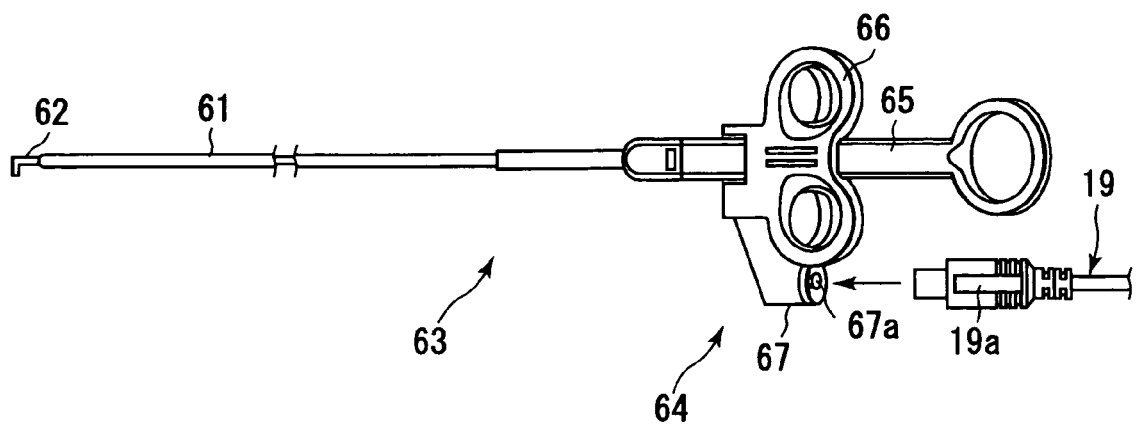
FIG. 15 is a perspective view of the main part of the sixth embodiment of the present invention.

FIG. 15 shows the sixth embodiment of the present invention. In this embodiment, the present invention is applied to a high frequency surgical instrument such as a diathermic knife 63, which has a hook-type electrode 62 as an electrode portion for the high frequency surgical instrument that is operated to project and withdraw from a distal end of an electric insulating sheath 61.

In this embodiment, a handle portion 64 of the diathermic knife 63 includes a substantially shaft-like main body 65 of the handle portion, as in the case of the diathermic snare 1 of the first embodiment (see FIGS. 1 to 7A), and a slider 66 that is mounted slidably along the axial direction of the main body 65 of the handle portion. Further, a plug 67 to which the connection cord 19 is detachably connected to an external high frequency power source that is not shown in the figure, as in the case of the first embodiment, is provided for one side of the slider 66. The plug 67 is provided with a contact pin (cord parallel connection portion) 67a that project in substantially parallel with the advancing/retreating direction of the slider 66.

The contact pin 67a is designed such that the connector 19a of the connection cord 19 is connected detachably thereto as the connector fits with the pin. Thus, the connector cord 19 is lead backwards in substantially parallel with the advancing/retreating direction of the slider 66 while the connector 19a of the connection cord 19 is connected to the contact pin 67a.

According to the structure of this embodiment, the contact pin 67a, which is made to project in substantially parallel with the advancing/retreating direction of the slider 66 as in the case of the handle portion 5 of the diathermic snare 1 of the first embodiment, is provided in the handle portion 64 of the diathermic knife 63. Thus, the central axis of the plug 67 to which the cord 19 is connected, is made in parallel with the central axis of the main body 65 of the handle portion. With this arrangement, as the connector 19a of the connection cord 19 is detachably fit with the contact pin 67a, the connection cord 19 is lead backwards in substantially parallel with the advancing/retreating direction of the slider 66 while the connector 19a of the connection cord 19 is connected to the contact pin 67a. In this manner, it is possible to prevent the cord 19 from entwining with the handle portion 64 even when the entire handle portion 64 is rotated in the direction of the rotation axis to re-direct the hook-type electrode 62 towards a desired direction for capturing living tissue in a body cavity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high frequency surgical instrument comprising:
a slender cylindrical electro-insulating sheath including a distal end and a proximal end;
a handle main body mounted to the proximal end of the sheath;
a slider configured to advance and retreat on the handle main body along an axial direction of the sheath;
an electrode portion for a diathermic treatment, configured to project from or withdraw into a distal end of the sheath in accordance with the advancing and retreating of the slider;
an electric connection portion provided in the slider, to which a connection cord for connection with an external high frequency power source, is detachably connected;
a conducting member configured to electrically connecting the electric connection portion and the electrode portion; and
a cord connection portion configured to lead the connection cord backwards along an advancing and retreating direction of the slider;
wherein the electric connection portion includes a connection portion rotating portion configured to connect the connection cord thereto rotatably in a direction of rotation of an axis of the connection cord.

2. A high frequency surgical instrument comprising:
a slender cylindrical electro-insulating sheath including a distal end and a proximal end;
a handle main body mounted to the proximal end of the sheath;
a slider configured to advance and retreat on the handle main body along an axial direction of the sheath;
an electrode portion for a diathermic treatment, configured to project from or withdraw into a distal end of the sheath in accordance with the advancing and retreating of the slider;

an electric connection portion provided in the slider, to which a connection cord for connection with an external high frequency power source, is detachably connected;
a conducting member configured to electrically connecting the electric connection portion and the electrode portion; and
a cord connection portion configured to lead the connection cord backwards along an advancing and retreating direction of the slider;
wherein the electric connection portion includes a plug to which the connection cord is mounted, and
the plug includes a contact pin, the contact pin being provided in parallel with the advancing and retreating direction of the slider.

3. A high frequency surgical instrument comprising:
a slender cylindrical electro-insulating sheath including a distal end and a proximal end;
a handle main body mounted to the proximal end of the sheath;
a slider configured to advance and retreat on the handle main body along an axial direction of the sheath;
an electrode portion for a diathermic treatment, configured to project from or withdraw into a distal end of the sheath in accordance with the advancing and retreating of the slider;
an electric connection portion provided in the slider, to which a connection cord for connection with an external high frequency power source, is detachably connected;
a conducting member configured to electrically connecting the electric connection portion and the electrode portion; and
a cord connection portion configured to lead the connection cord backwards along an advancing and retreating direction of the slider;
wherein the electric connection portion further comprises:
a vertical plug projecting in a vertical direction that is normal to the advancing and retreating direction of the slider; and
a conversion plug configured to change a direction of the plug in a direction in parallel to the advancing and retreating direction of the slider, the plug being coupled detachably to the vertical plug;
the vertical plug includes a contact pin projecting in a vertical direction that is normal to the advancing and retreating direction of the slider;
the conversion plug includes a plug main body having a shape bent into substantially a letter L;
the plug main body further includes: a main body-side connection portion projecting from one of the bent shape of the letter L; and
a cord-side connection portion projecting from an other one of the bent shape of the letter L; and
the cord connection portion includes a contact pin formed to project in substantially parallel with the advancing and retreating direction of the slider, and to which the connection cord is detachably connected.

4. A high frequency surgical instrument comprising:
a slender cylindrical electro-insulating sheath including a distal end and a proximal end;
a handle main body mounted to the proximal end of the sheath;
a slider configured to advance and retreat on the handle main body along an axial direction of the sheath;
an electrode portion for a diathermic treatment, configured to project from or withdraw into a distal end of the sheath in accordance with the advancing and retreating of the slider;
an electric connection portion provided in the slider, to which a connection cord for connection with an external high frequency power source, is detachably connected;
a conducting member configured to electrically connecting the electric connection portion and the electrode portion; and
a cord connection portion configured to lead the connection cord backwards along an advancing and retreating direction of the slider;
wherein the electric connection portion includes a vertical plug formed to project in a vertical direction that is normal to the advancing and retreating direction of the slider, and
the connection cord includes an L-shaped connector detachably connected to the vertical plug, the connector being bent into substantially an L-shape.

* * * * *